(12) United States Patent
Liotta et al.

(10) Patent No.: US 10,324,008 B2
(45) Date of Patent: Jun. 18, 2019

(54) COMPOSITIONS AND METHODS FOR LASER CAPTURE MICRODISSECTION

(71) Applicant: GEORGE MASON UNIVERSITY, Fairfax, VA (US)

(72) Inventors: Lance Liotta, Bethesda, MD (US); Virginia Espina, Rockville, MD (US); Nitin Agrawal, Fairfax, VA (US); Alessandra Luchini, Burke, VA (US)

(73) Assignee: GEORGE MASON RESEARCH FOUNDATION, Fairfax, VA (US)

( * ) Notice: Subject to any disclaimer, the term of this patent is extended or adjusted under 35 U.S.C. 154(b) by 224 days.

(21) Appl. No.: 15/388,919

(22) Filed: Dec. 22, 2016

(65) Prior Publication Data
US 2017/0176301 A1 Jun. 22, 2017

Related U.S. Application Data

(60) Provisional application No. 62/271,027, filed on Dec. 22, 2015.

(51) Int. Cl.
*G01N 1/00* (2006.01)
*G01N 1/28* (2006.01)

(52) U.S. Cl.
CPC ..... *G01N 1/2813* (2013.01); *G01N 2001/284* (2013.01)

(58) Field of Classification Search
CPC .................................................... G01N 1/00
See application file for complete search history.

(56) References Cited

U.S. PATENT DOCUMENTS 7,488,169 B2 * 2/2009 Keduka .................. B29C 51/24
264/299

OTHER PUBLICATIONS

Espina, V. et al., Laser-Capture Microdissection. Nat Protoc. 2006; 1(2):586-603.
Mengüç, Y. et al., Gecko-Inspired Controllable Adhesive Structures Applied to Micromanipulation. Adv Funct Mater. 2012; 22(6):1246-54.
U.S. Appl. No. 62/271,027, filed Dec. 22, 2015, Lance Liotta (George Mason University).

* cited by examiner

*Primary Examiner* — Jyoti Nagpaul
(74) *Attorney, Agent, or Firm* — Ballard Spahr LLP

(57) ABSTRACT

Compositions and methods for the simultaneous capture and release using micropattern surfaces for tissue and cell microdissection. In one example, a patterned thermoplastic film has a first surface and a plurality of projections attached to and extending outwardly from the first surface. The projections form a pattern on the thermoplastic film.

19 Claims, 8 Drawing Sheets

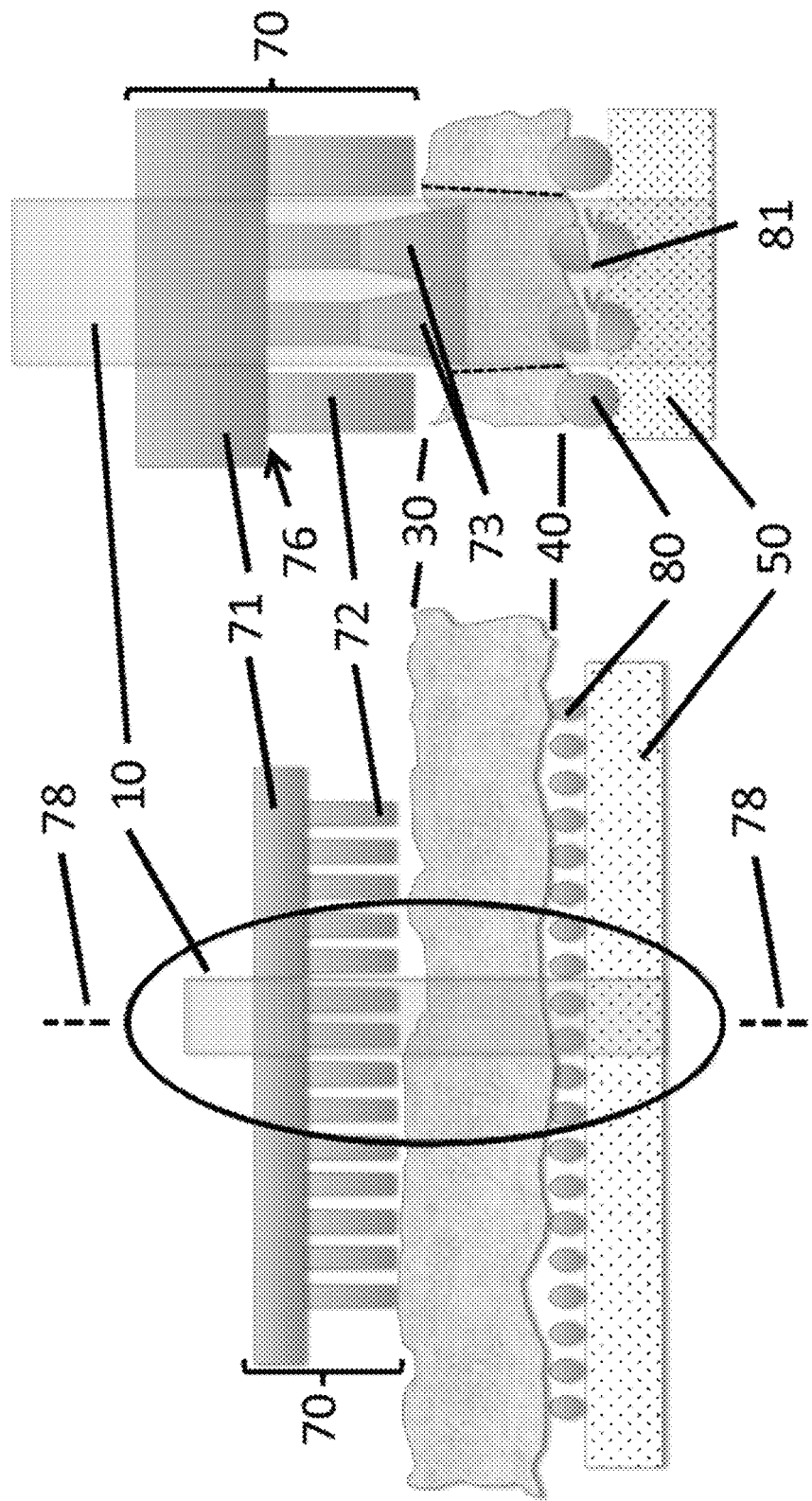

ered by the National Institutes of Health. The government has certain rights in the invention.

COMPOSITIONS AND METHODS FOR LASER CAPTURE MICRODISSECTION

CROSS-REFERENCE TO RELATED PATENT APPLICATION

This application claims priority to and the benefit of the filing date of U.S. Provisional Patent Application No. 62/271,027, filed Dec. 22, 2015, the content of which is hereby incorporated by reference herein in its entirety.

STATEMENT REGARDING FEDERALLY FUNDED RESEARCH

This invention was made with government support under grant number 1R33CA173359-03 awarded by the National Institutes of Health. The government has certain rights in the invention.

BACKGROUND

Laser Capture Microdissection ("LCM") is an established technology used to pluck out tumor cells, or other types of cells, from a heterogeneous piece of tissue under direct microscopic visualization. The procured cells are used in commercial diagnostic assays, clinical trials, and research studies by pharma and academia. LCM is used by thousands of scientists worldwide. The most popular, and most useful, form of LCM employs a laser beam or a source of radiation to heat a flat plastic film that is held against the slice of tissue mounted on a glass slide (FIG. 1A). The plastic film is uniformly impregnated with a dye that absorbs laser energy. The region of the plastic film positioned over the tissue region or cell of interest is selectively heated by the radiation causing this region to melt and embed itself into the tissue segment immediately underneath (FIG. 1B). When the film is lifted off the tissue the portions of the tissue adherent to the undersurface of the film are ripped free of the tissue section (e.g., see Espina V., et al. (2006) Nature Prot. 1(2):586-603).

Despite the power and utility of LCM, the method is currently limited by a number of shortcomings. First, currently available LCM methods suffer from the variability in the capture efficiency of the desired region of the tissue. The variability is caused by a reduced adhesive force on the top of the tissue section between the tissue and the film and an increased adhesive force between the tissue section and the glass slide substratum. Second, the resolution of LCM systems is limited because the film melts against the tissue in a variable manner depending on the focus of the laser beam, the surface contours, and the wavelength of the light. An area spanning many tissue cell diameters is often captured, thus limiting the resolution and preventing the precise capture of single cells or components of cells.

Despite advances in methods and composition pertaining LCM, there remain significant drawbacks to the methods which limit the use and application of LCM. These needs and other needs are satisfied by the present disclosure.

SUMMARY

In accordance with the purpose(s) of the disclosure, as embodied and broadly described herein, the disclosure, in one aspect, relates to compositions and methods for laser capture microdissection. In various aspects, the present disclosure pertains to compositions and methods for the simultaneous capture and release using micropattern surfaces for tissue and cell microdissection.

Disclosed herein are patterned (e.g., micropatterned) thermoplastic films comprising projections that are attached to, continuous with, or integrally formed with a surface of the micropatterned thermoplastic film. In various aspects, a patterned thermoplastic film can have a first surface and a plurality of projections secured to and extending outwardly from the first surface, with the projections forming a pattern on the thermoplastic film.

Also disclosed are methods for laser capture microdissection, comprising the steps of: (a) placing a disclosed micropatterned thermoplastic film in contact with a tissue sample, and (b) irradiating the micropatterned thermoplastic film in contact with the tissue sample with electromagnetic radiation in the UV or IR spectrum.

Also disclosed are kits including a disclosed micropatterned thermoplastic film and instructions for using the film in a laser capture microdissection. In an aspect, it is contemplated that the kits can further comprise ingredients for producing the micropatterned thermoplastic film. In another aspect, it is contemplated that the kits can further comprise dyes and/or applicators for producing or using the disclosed micropatterned thermoplastic films.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the disclosure.

FIGS. 2A-2C show exemplary components of the disclosed apparatus, which includes a patterned thermoplastic film. FIG. 2A depicts a patterned thermoplastic film prior to contact with tissue as disclosed herein. FIG. 2B depicts the patterned thermoplastic film in contact with the tissue as UV or IR laser irradiation is applied. FIG. 2C shows an expanded close-up view of the area within the oval of FIG. 2B.

FIG. 3A schematically depicts an increase in adhesive contact with tissue at the tip of a projection as disclosed herein. FIG. 3B schematically depicts the activation of "microneedle" projections as disclosed herein to form an expanded tip anchor.

FIG. 4A schematically depicts non-adhesive nanoparticles, which are shed from an activated projection or tip of the micropatterned surface as the projection expands and contacts the tissue upper surface but not the the lower tissue surface. FIG. 4B schematically depicts the breaking of the shell of an adhesive nanoparticle to make the nanoparticle non-adhesive, thereby dissociating crosslinks in the shell in response to interaction with an IR or UV laser beam. FIG. 4C schematically depicts the breaking of the hydrophobic non-adhesive shell of a nanoparticle in response to interaction with an IR or UV laser beam to expose an inner adhesive core.

FIGS. 5A and 5B show representative fabricated micropattern surfaces that were produced by an inverted photolithography mold applied to the thermopolymer surface to form the micropattern surface. FIG. 5C is an image of a standard cap component where the thermopolymer surface was mounted. FIG. 5D shows that that tips of projections (e.g., micropillars) formed by these methods can be wetted by water while the base remains repulsive and non-wetted by the water.

Figure 1A:
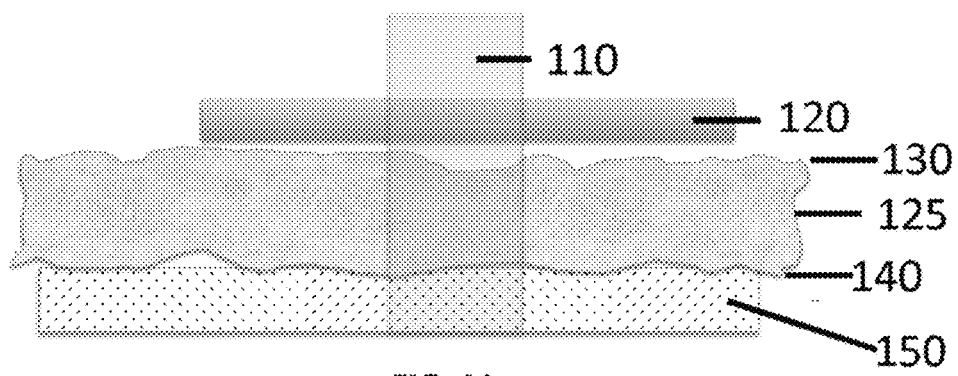
FIG. 1A depicts a typical LCM system, which includes a thermoplastic film placed in contact with an upper surface of tissue, which has an undersurface that is mounted on a glass slide.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DESCRIPTION

The present disclosure can be understood more readily by reference to the following detailed description of the disclosure and the Examples included therein.

As used in the specification and the appended claims, the singular forms "a," "an" and "the" include plural referents unless the context clearly dictates otherwise. Thus, for example, reference to "a projection" can include two or more such projections unless the context indicates otherwise.

All technical and scientific terms used herein have the same meaning as commonly understood to one of ordinary skill in the art to which this invention belongs unless clearly indicated otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

The purpose of the laser capture microdissection ("LCM") technique is to provide a simple method for the procurement of selected human cells from a heterogeneous population contained on a typical histopathology biopsy slide. A typical tissue biopsy sample consists of a 5 to 10 micron slice of tissue that is placed on a glass microscope slide using techniques well known in the field of pathology. This tissue slice is a cross section of the body organ that is being studied. The tissue consists of a variety of different types of cells. Often a pathologist desires to remove only a small portion of the tissue for further analysis.

Figure 1B:
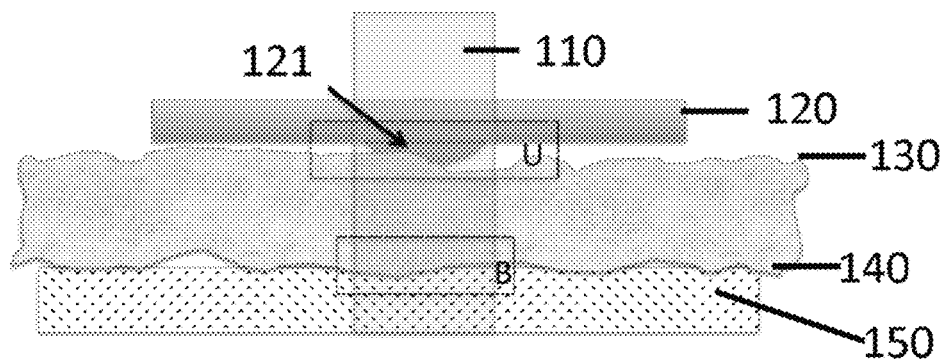
FIG. 1B schematically depicts activation of the thermoplastic film by laser enerty, causing the film to locally melt and become embedded at the tissue surface.

FIGS. 1A and 1B show typical LCM components. As shown in FIGS. 1A and 1B, the components can include a thermoplastic film 120 that is placed in contact with an upper surface 130 of the tissue 125, while the undersurface 140 of the tissue is mounted on a glass slide 50. Activation of the film by laser energy 110 causes the film to locally melt an area 121 beneath the thermoplastic film 120 that is in the beam of the laser energy 110. The melted area of the film 121 embeds at the tissue surface. The film 120 is then removed and thereby tears away the tissue portion immediately below the locally melted film area 121. The success of this operation is dependent on the balance of forces above the selected region of interest (in region "U") and below the selected region of interest (in region "B").

In various aspects of the present disclosure, LCM can be employed using a patterned (e.g., micropatterned) thermoplastic transfer film comprising projections, such as micropillars, micro projections, hydrogel microspheres, and/or microneedles as further disclosed herein, that are attached to, continuous with, or integrally formed with a thermoplastic film, that is placed on top of the tissue sample. This film and/or the projections can be manufactured containing organic dyes that are chosen to selectively absorb in the ultraviolet or infrared region of the spectrum overlapping the emission region of common laser diodes, e.g., AlGaAs laser diodes. In an aspect, when the film is exposed to the focused laser beam the exposed region is heated by the laser and melts, adhering to the tissue in the region that was exposed. The film is then lifted from the tissue and the selected portion of the tissue is removed with the film. As further disclosed herein, it is contemplated that the disclosed compositions and methods can increase the adhesive strength and improve the resolution of the film in contact with the tissue surface while at the same time selectively reducing the adhesive forces on the bottom of the tissue, where it can be tightly dried down on the glass slide.

Figure 2A:
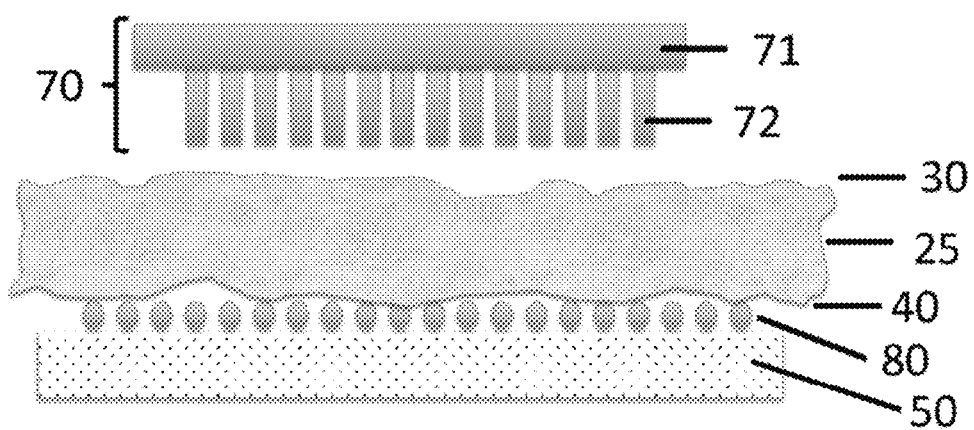

In an aspect, and with reference to FIGS. 2A-4A, a micropatterned thermoplastic film 70 comprises projections 72, such as micropillars, micro projections, hydrogel microspheres, and/or microneedles that are attached to, continuous with, or integrally formed with a thermoplastic film layer 71 that defines a first (e.g., bottom) surface 76. In a further aspect, the projections 72 (e.g., micropillars, micro projections, hydrogel microspheres, and/or microneedles as disclosed herein) form an array on a surface (e.g., the first surface 76) of the micropatterned thermoplastic film. In some aspects, the projections 72 (e.g., micropillars, micro projections, hydrogel microspheres, and/or microneedles) are formed on a single surface of a planar or substantially planar thermoplastic film layer 71, and an opposing surface of the substantially planar thermoplastic film layer can be substantially smooth or lacking projections (e.g., micropillars, micro projections, hydrogel microspheres, and/or microneedles). Optionally, as shown in FIGS. 2A-2C, the projections 72 can extend outwardly from the first surface 76 of the patterned thermoplastic film layer 71 relative to an axis 78 that is perpendicular or substantially perpendicular to the first surface. As used herein, the term "micropatterned" refers to thermoplastic films that are patterned with projections as further disclosed herein.

In an aspect, the micropatterned thermoplastic film 70 can comprise an array of projections 72 that cooperate to define a pattern on a surface of the film. In this aspect, it is contemplated that the projections 72 of the array can comprise micropillars, micro projections, hydrogel microspheres, microneedles, or combinations thereof. As used herein, the term "micropillar" refers to a projection that, prior to activation as disclosed herein, has a consistent or substantially consistent outer diameter along its length. As used herein, the term "microsphere" refers to a projection that, prior to activation as disclosed herein, has a generally rounded appearance, including spherical, substantially spherical, ovoid, and substantially ovoid shapes. As used herein, the term "microneedle" refers to a projection that, prior to activation as disclosed herein, has a diameter that decreases (optionally, consistently decreases) moving away from the first surface 76 of the patterned thermoplastic film. It is contemplated that the "micropillars" and "microneedles" can have any desired cross-sectional shape, including, for example and without limitation, circular, square, rectangular, triangular, oval, elliptical, trapezoidal, pentagonal, hexagonal, heptagonal, or octagonal shapes. Optionally, as shown in FIG. 3B, a microneedle can have a pointed distal tip. In an aspect, at least one of the projections of the array can have a consistent diameter. Optionally, in this aspect, at least two of the projections can have a consistent diameter. In a further aspect, each projection of the plurality of projections can have a consistent diameter. In another aspect, at least one of the projections can have a variable diameter that increases or decreases moving away from the first surface 76 of the patterned thermoplastic film. Optionally, in this aspect, at least two of the projections can have a variable diameter. In a further aspect, each projection of the plurality of projections can have a variable diameter. In one exemplary aspect, it is contemplated that each projection of the plurality of projections can be a micropillar. In another exemplary aspect, it is contemplated that each projection of the plurality of projections can be a microsphere. In another exemplary aspect, it is contemplated that each projection of the plurality of projections can be a microneedle. In still another exemplary aspect, it is contemplated that the plurality of projections can comprise at least one micropillar and at least one microneedle. In still another exemplary aspect, it is contemplated that the plurality of projections can comprise at least one micropillar and at least one microsphere. In still another exemplary aspect, it is contemplated that the plurality of projections can comprise at least one microsphere and at least one microneedle. In still another exemplary aspect, it is contemplated that the plurality of projections can comprise at least one micropillar, at least one microneedle, and at least one microsphere.

In an aspect, the projections 72 of the micropatterned thermoplastic film 70 can have a width or outer diameter ranging from about 1 nm to about 10 mm and a length ranging from about 1 nm to about 10 mm. As one will appreciate, the length of each projection 72 can correspond to the height of the projection relative to the first surface 76 of the micropatterned thermoplastic film 70. In exemplary aspects, the width or outer diameter and the length of each projection can both range from about 100 nm to about 1 mm. Thus, in these aspects, it is contemplated that the width or outer diameter can be about 100 nm, about 200 nm, about 300 nm, about 400 nm, about 500 nm, about 600 nm, about 700 nm, about 800 nm, about 900 nm, about 1 μm, about 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, about 300 μm, about 400 μm, about 500 μm, about 600 μm, about 700 μm, about 800 μm, about 900 μm, or about 1 mm, or can fall within a range defined between any two of these listed values. Optionally, in exemplary aspects, it is contemplated that the length of each projection 72 can be greater than the width or outer diameter of the projection. In one exemplary aspect, the projections 72 can each have a diameter of about 100 μm, and the projections can be fabricated such that each of the projections has a consistent (equal or substantially equal) height ranging from about 10 μm to about 100 μm.

During fabrication of the pattern, it is contemplated that the projections 72 can be fabricated to have any desired spacing relative to other projections (e.g., adjacent projections) within the array. Optionally, in some aspects, the projections 72 can have an equal or substantially equal spacing within the array (measured between center points of the respective projections). For example, it is contemplated that the projections 72 can be organized in columns, rows, or combinations thereof, in which each projection is spaced from adjacent projections by a consistent distance, such as, for example and without limitation, a distance ranging from about 10 μm to 1 mm and, more preferably, from about 10 μm to about 200 μm, or about 100 μm. However, in other aspects, it is contemplated that the projections can be fabricated to have a variable spacing, with at least one projection being closer to some adjacent projections than others. In these aspects, it is contemplated that portions of the array can have a higher concentration of projections than other projections. It is further contemplated that the array of projections can include at least one projection having a width or outer diameter that is different than the width or outer diameter of at least one other projection. Optionally, it is contemplated that the projections can include projections having three or more different widths or outer diameters. It is still further contemplated that the array of projections can include at least one projection having a length that is different than the length of at least one other projection. Optionally, it is contemplated that the projections can include projections having three or more different lengths.

As used herein, in the context of spacing between projections, "adjacent" does not indicate physical contact; instead, the term "adjacent" refers to the projection in closest proximity to a given projection relative to a particular reference axis. For example, if projections are arranged in a row, then a selected projection may be adjacent to the two projections within the row on either side of the selected projection. If the selected projection is also arranged within a column of projections, then the selected projection may also be adjacent to the two projections within the column on either side of the selected projection.

In an aspect of the present disclosure, the projections are formed on a film using a photolithography mold that is applied to the thermopolymer surface mounted on a cap. In a further aspect, the micropatterned thermoplastic transfer film can be a film such as a 100 micron thick ethyl vinyl acetate (EVA) film available from Electroseal Corporation of Pompton Lakes, N.J. (type E540), on which projections have been formed, e.g., using a photolithography mold. The film is chosen to have a suitable melting point, e.g., from about 70° C. to about 120° C. In an aspect, the melting point of the film is about 90° C.

The micropattern thermoplastic films of the present disclosure can be any suitable thermoplastic. For example, the micropattern thermoplastic film can be fabricated from one or more of: EVAs; polyurethanes (PU); polyvinyl acetates; ethylene-methyl acrylate (EMAC); polycarbonate (PC); ethylene-vinyl alcohol copolymers (EVOH); polypropylene (PP); and expandable or general purpose polystyrene (PS). ELVAX 410, 200 and 205 are suitable resins of EVA that are commercially available from DuPont wherein the operative variant is the amount of vinyl.

In an aspect, micropatterned thermoplastic film, such as an EVA film, used in LCM techniques can comprise an absorptive substance. The absorptive substance can include an absorptive dye. This dye can be either a broad band absorptive dye or a frequency specific absorptive dye. For example, the absorptive dyes can include one or more of: tin(IV) 2,3-naphthalocyanine dichloride; silicon(IV) 2,3-naphthalocyanine dihydroxide; silicon (IV) 2,3-naphthalocyanine dioctyloxide; and vanadyl 2,11,20,29-tetra-tert-butyl-2,3-naphthalocyanine. The absorptive dye can be an infrared napthalocyanine dye, available from Aldrich Chemical Company (dye number 43296-2 or 39317-7). Also, the absorptive substance can include a plurality of fullerines (i.e., Bucky Balls, e.g., C60). An absorptive substance can have a strong absorption in the 800 nm region, a wavelength region that overlaps with laser emitters used to selectively melt the film. The absorptive substance is mixed with the melted bulk plastic at an elevated temperature. The thermoplastic comprising the absorptive substance is then manufactured into a film using standard film manufacturing techniques. The dye concentration in the plastic can be about 0.001 M.

The micropatterned thermoplastic film of the present disclosure can further comprise a scattering media. Since the micropatterned thermoplastic film is very close to the sample, the scattering media reduces shadows, and can thereby improving the process of imaging. The scattering media can include a diffusing material. For example, the micropatterned thermoplastic film can be loaded with a small particulate material that scatters the illumination light so as to minimize shadows and improve imaging without detrimentally effecting the LCM beam. Alternatively, the micropatterned thermoplastic film can include a dichromatic gelatin (DCG) to perform the same functions. The DCG can be exposed and developed to provide specific diffuser properties within the transfer film such as shaping.

The micropatterned thermoplastic films of the present disclosure are used with appropriate laser sources. For example, suitable laser pulse widths are from 0 to approximately 1 second, preferably from 0 to approximately 100 milliseconds, more preferably approximately 50 milliseconds. In a preferred embodiment the wavelength of the laser is 810 nm. In a preferred embodiment the spot size of the laser at the EVA material located on microcentrifuge tube cap 120 is variable from 0.1 to 100 microns, preferably from 1 to 60 microns, more preferably from 5 to 30 microns. These ranges are relatively preferred when designing the optical subsystem. From the standpoint of the clinical operator, the widest spot size range is the most versatile. A lower end point in the spot size range on the order of 5 microns is useful for transferring single cells.

Suitable lasers can be selected from a wide power range. For example, a 100 watt laser can be used. On the other hand, a 50 mW laser can be used. The laser can be connected to the rest of the optical subsystem with a fiber optical coupling. Smaller spot sizes are obtainable using diffraction limited laser diodes and/or single mode fiber optics. Single mode fiber allows a diffraction limited beam.

Changing the beam diameter permits the size of the portion of the sample that is acquired to be adjusted. Given a tightly focused initial condition, the beam size can be increased by defocusing. Given a defocused initial condition, the beam size can be decreased by focusing. The change in focus can be in fixed amounts. The change in focus can be obtained by means of indents on a movable lens mounting and/or by means of optical glass steps. In any event, increasing/decreasing the optical path length is the effect that is needed to alter the focus of the beam, thereby altering the spot size. For example, inserting a stepped glass prism 380 into the beam so the beam strikes one step tread will change the optical path length and alter the spot size.

As shown in FIGS. 2A-2B, the disclosed apparatus can replace two components of the conventional LCM capture technology with new materials. As further disclosed herein, the top film of conventional LCM technology, which is flat and smooth, can be replaced by a micropatterned thermoplastic film comprising projections having surfaces that can be activated by selective radiant energy, such as from a laser beam, to become adhesive to the irregular tissue surface 30 below. Additionally, as further disclosed herein, the glass slide 50 that the tissue is mounted on can also be modified by coating it with microparticles or nanoparticles that can be altered in their tissue adhesive properties by UV or IR laser irradiation (FIG. 2A) When the laser irradiation takes place over the desired region of the tissue 25, the adhesive capture is activated above the tissue and dissolved below the tissue (FIGS. 2B and 2C). This addresses both sources of variability to achieve a higher efficiency, yield, and resolution, with no changes to the overall operation of the other components of the LCM instrumentation.

FIGS. 2A-2C show exemplary components of the LCM of the present disclosure. FIG. 2C shows an expanded view of the area within the oval of FIG. 2B. As shown in FIGS. 2A-2C, the smooth film 120 depicted in FIGS. 1A and 1B, which is typically used, is replaced by a micropatterned thermoplastic film 70 comprising projections 72, such as micropillars, micro projections, hydrogel microspheres, and/or microneedles, that are attached to, continuous with, or integrally formed with a thermoplastic film surface 71. The projections can conform to the upper tissue surface 30 and increase the adhesive forces to the irregular tissue surface below when activated by UV or IR laser irradiation 10. The increased adhesive forces are due, at least in part, to an expanded projection tip 73 that occurs upon activation by UV or IR laser irradiation 10. The laser irradiation is directed over the desired region of tissue 25, and the laser irradiation activates the adhesive capture above the tissue. The lower surface 40 of the tissue 25, instead of directly resting on the glass slide 50, rests on a microparticle or nanoparticle coating 80 that can be altered in its adhesive properties by the laser energy alone or in combination with a chemical treatment 81 of the tissue 25. The laser energy simultaneously activates the adhesive forces on the top face while breaking or dissolving the adhesive force below 81. This achieves high efficiency and precision of capture with lower non specific capture.

Figure 3A:
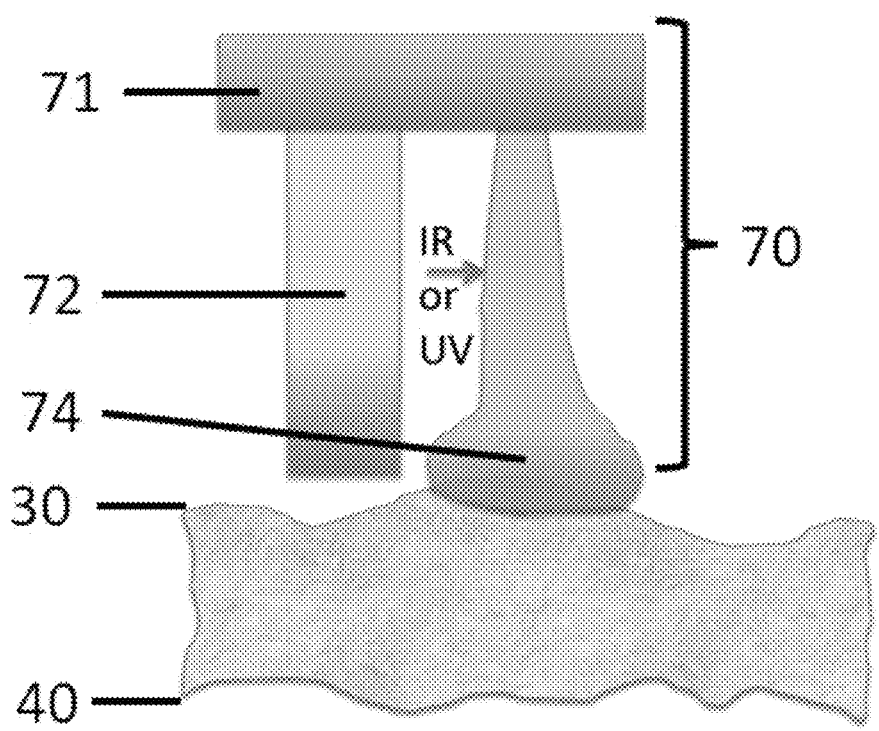
FIGS. 3A and 3B show configurable aspects of projections of patterned thermoplastic film as disclosed herein.
Figure 3B:
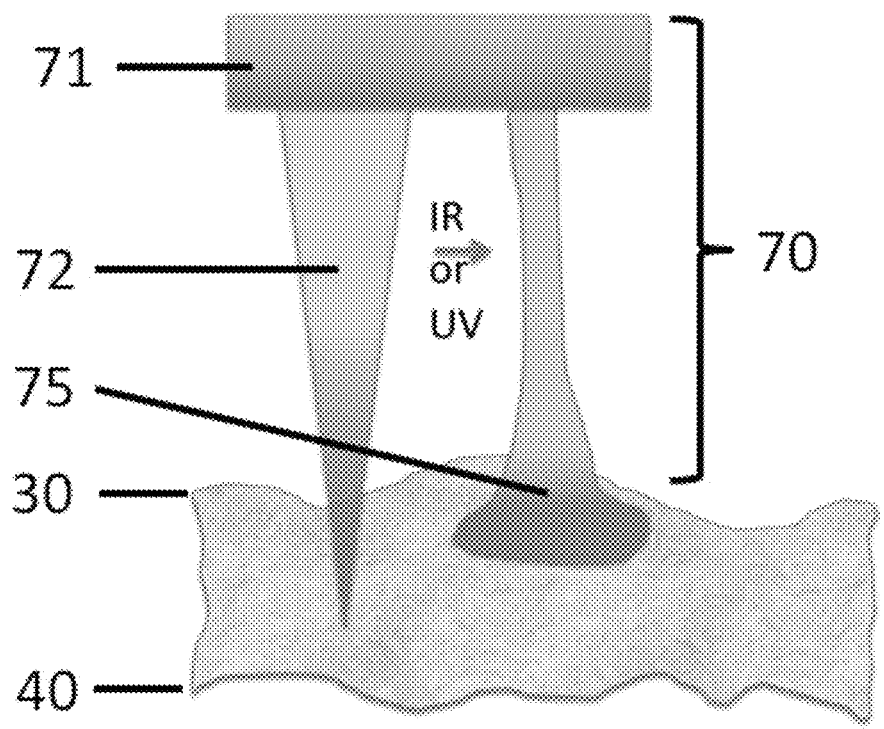

FIGS. 3A and 3B show configurable aspects of the micropatterned surface projections 72. In both FIGS. 3A and 3B, the micropatterned thermoplastic film 70 comprises projections 72, such as micropillars, micro projections, hydrogel microspheres, and/or microneedles, that are attached to or continuous with a thermoplastic film layer 71 as disclosed herein. The projections 72 can be impregnated with a UV or IR absorbing dye in a gradient concentrated at the distal tip of the projections or pillars. In one aspect, as shown in FIG. 3A, activation by the laser can expand and increase the adhesive contact with the surface only at the tip 74. In an alternative aspect, as shown in FIG. 3B, projections 72 in the form of thermoplastic needles can be activated to engage (e.g., grab onto) the tissue with an expanded tip anchor 75. The upper surface 30 of the tissue 25 and the undersurface 40 of the tissue can have the same characteristics depicted and described with respect to FIGS. 2A-2B.

The use of micro or nanopillar patterning massively enhances the adhesive force as has been shown for Gecko feet dry adhesion models (Menguc et al Advanced Functional Materials 2012, 22, 1246-1254) while at the same time improving the resolution to achieve a capture area defined by the narrowest micropillar diameter. The laser energy can activate the micropillars to become adhesive by various means as shown in FIGS. 3A-3B. By impregnating the micropillar with a gradient of a UV or IR absorbing dye the tip can be made to swell and conform to the tissue surface irregularities (FIG. 3A) selectively at the tip. The diameter of the pillar strictly confines the region of resolution. Alternatively, the micropillar can be a micro needle with a concentration of the dye in the tip that penetrates into the tissue and is then permanently anchored into the tissue (below the surface) by the laser energy (FIG. 3B).

Figure 4A:
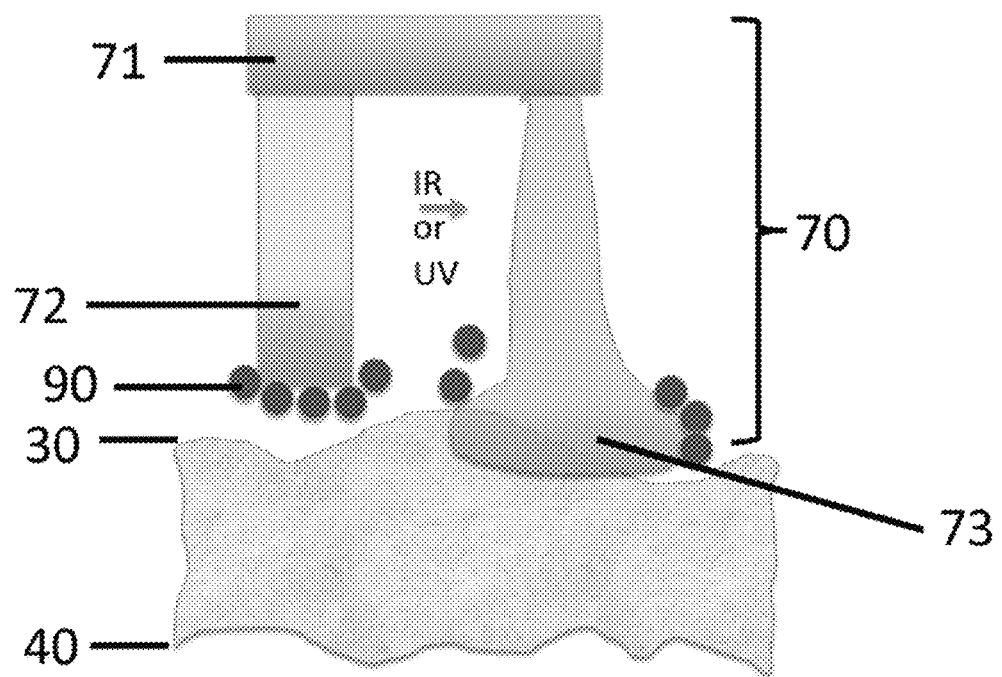
FIGS. 4A-4C show configurable aspects of hydrogel nanoparticles positioned on projections of a patterned thermoplastic film as disclosed herein.
Figure 4B:
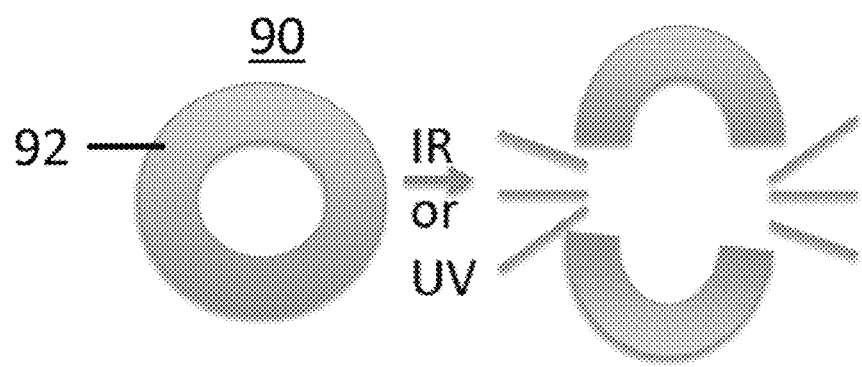
Figure 4C:
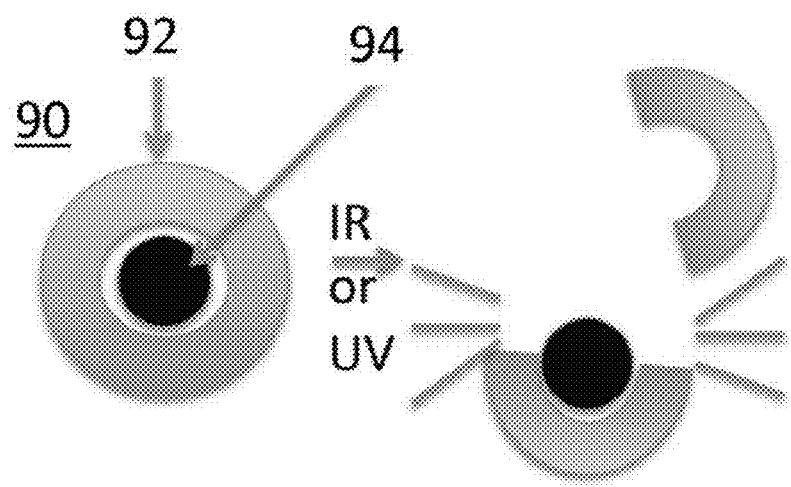

FIGS. 4A-4C show configurable aspects of hydrogel particles (e.g., nanoparticles), which can be provided on at least one surface of the projections 72. The hydrogel particles can be deformable and can be configured to modify the adhesive properties of the system. FIG. 4A shows non-adhesive particles 90 that are shed from an activated projection 72 or tip of the micropatterned film 70, as the projection expands and contacts the tissue upper surface 30 but not the lower tissue surface 40. FIG. 4B shows schematically that the an adhesive particle can be made non-adhesive by breaking the shell 92 or polymer mesh of the particle by dissociating crosslinks in the shell or polymer mesh by interacting with an IR or UV laser beam. FIG. 4C shows an alternative configuration for the particle wherein the shell has a hydrophobic non-adhesive character, and upon interaction with an IR or UV laser beam, the non-adhesive hydrophobic shell is shed to expose an inner adhesive core 94.

In various aspects, both the upper and lower surface of the tissue can be in contact with surface with tunable adhesive properties. In one aspect, the tip of the projection (e.g., micropillar) structure 72 can be coated with nanoparticles or microparticles as shown in FIG. 4A. In a further aspect, the slide surface can be coated with nanoparticles or microparticles as shown in FIGS. 2A-2C. The nanoparticles or microparticles provide a means of modifying the adhesive properties, and as shown, can be localized at one or both surfaces of the tissue sample 25. For example, as shown in FIG. 4A, the tip of the projection (e.g., micropillar) structure can be activated by the laser energy to shed a non-adhesive microparticle coating or to activate a microparticle coating to become adhesive. In an aspect, an example of modifiable nanoparticles is hydrogel particles with reversible crosslinks that can open up in response to activation (see FIG. 4C). Once open they can expose an inner core 94 containing a covalently bound dye that is adhesive. Alternatively, in a further aspect, an adhesive particle with dissociating crosslinks is converted to a non-adhesive material by breaking of the shell 92 or polymer mesh using laser-activated dissociation as shown in FIG. 4B. In various aspects, nanoparticles or microparticles can also be coated onto the glass slide, thus provide a tunable adhesive surface on the lower surface 40 of the tissue 25.

A. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

An example of the micropatterned thermoplastic film of the present disclosure was prepared and characteristics are shown in FIGS. 5A-5F. In this example, the fabricated micropillars were formed on the surface of the film and impregnated with IR absorbing dyes. The tips of the micropillars can be made to be wetted (FIG. 5D) and the charge on the surface of the tips and the base of the micropillars can be differentially charged by plasmon surface coating. The overall goal is to create a micro- or nano-structured modification of the standard disposable components of conventional LCM systems, such as the Thermo Arcturus LCM system. Although these materials can have other uses, a particular use is to provide a significant improvement on performance that can be sold as new disposables for the LCM instruments that already exist throughout the world.

The LCM caps with pillar structures were fabricated utilizing a simple replica molding procedure. Initially, utilizing standard soft lithography methods, a negative block of polymer polydimethylsiloxane (PDMS) was created containing 10 μm deep wells of desired dimensions. Subsequently, the PDMS block was placed on a hot plate preheated to 125° C. and a blank LCM cap is placed in close contact with the patterned surface of PDMS. A dead weight was placed on top of the cap to keep it pressed against the PDMS wells. After 15-20 minutes of replica molding, the composite device was allowed to cool down to room temperature and the LCM cap containing pillar structures was separated from the PDMS block.

Figure 5A:
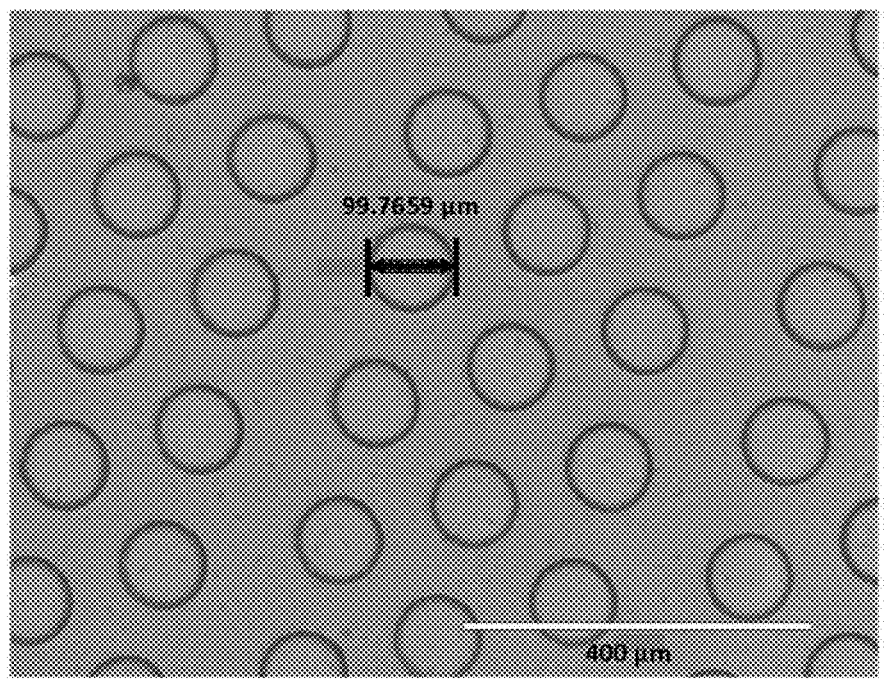
FIGS. 5A-5D show representative components of exemplary fabricated micropattern surfaces.
Figure 5B:
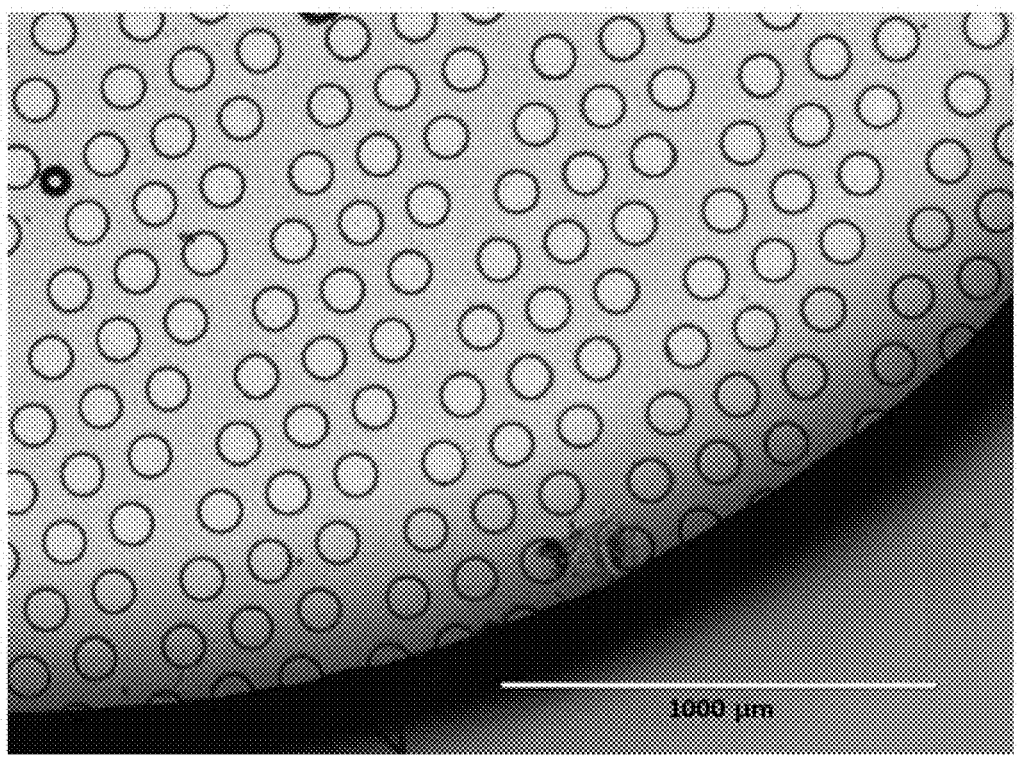
Figure 5C:
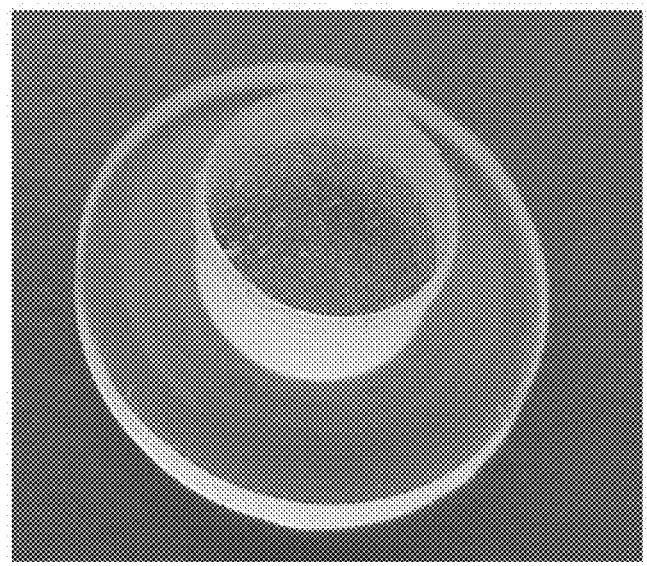
Figure 5D:
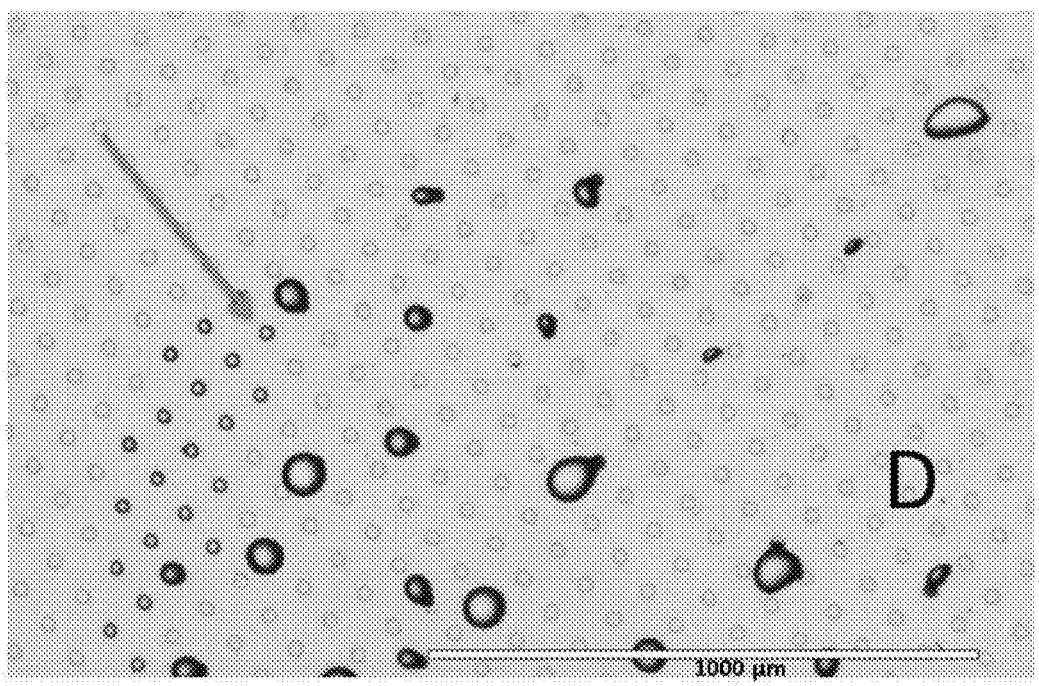

A photomicrograph of a fabricated micropattern surface is shown in FIGS. 5A and 5B. The photomicrograph was produced by an inverted photolithography mold applied to the thermopolymer surface mounted on a standard cap (FIG. 5C) for LCM on a Thermo Arcturus Instrument. FIGS. 5A and 5B show the uniformity of example micropillars that can be fabricated in any desired density and size. FIG. 5D shows how the tips of the micropillars can be made wetted by a minute drop of water while the base remains repulsive and non-wetted.

Figure 5E:
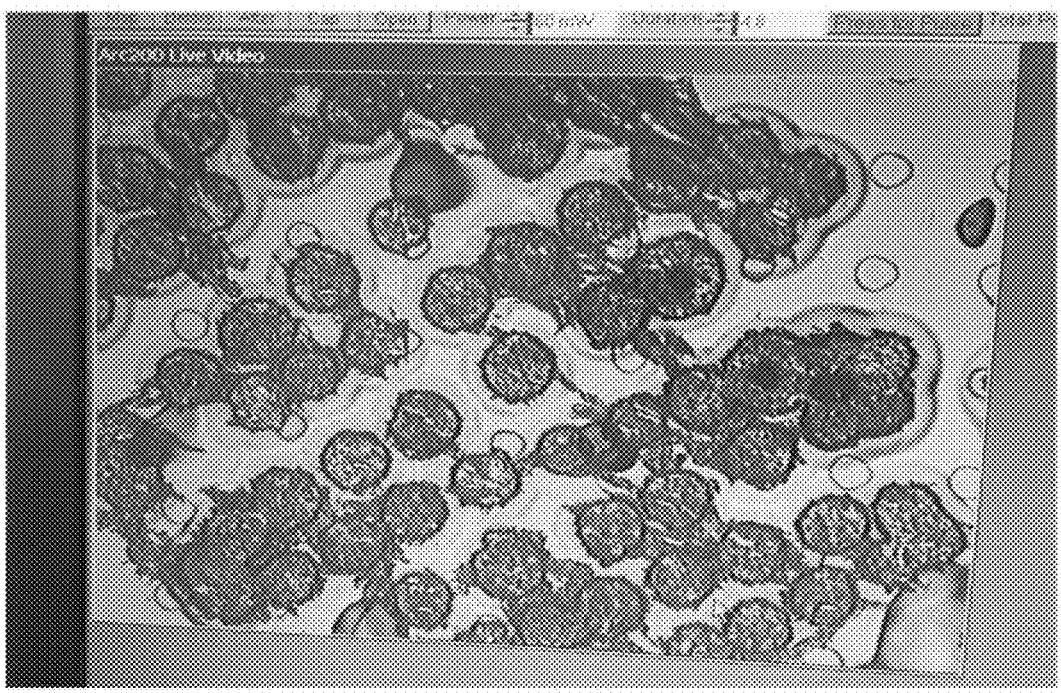
FIGS. 5E and 5F are representative microscopic images of captured cells using the micropattern surfaces of FIGS. 5A and 5B, respectively.
Figure 5F:
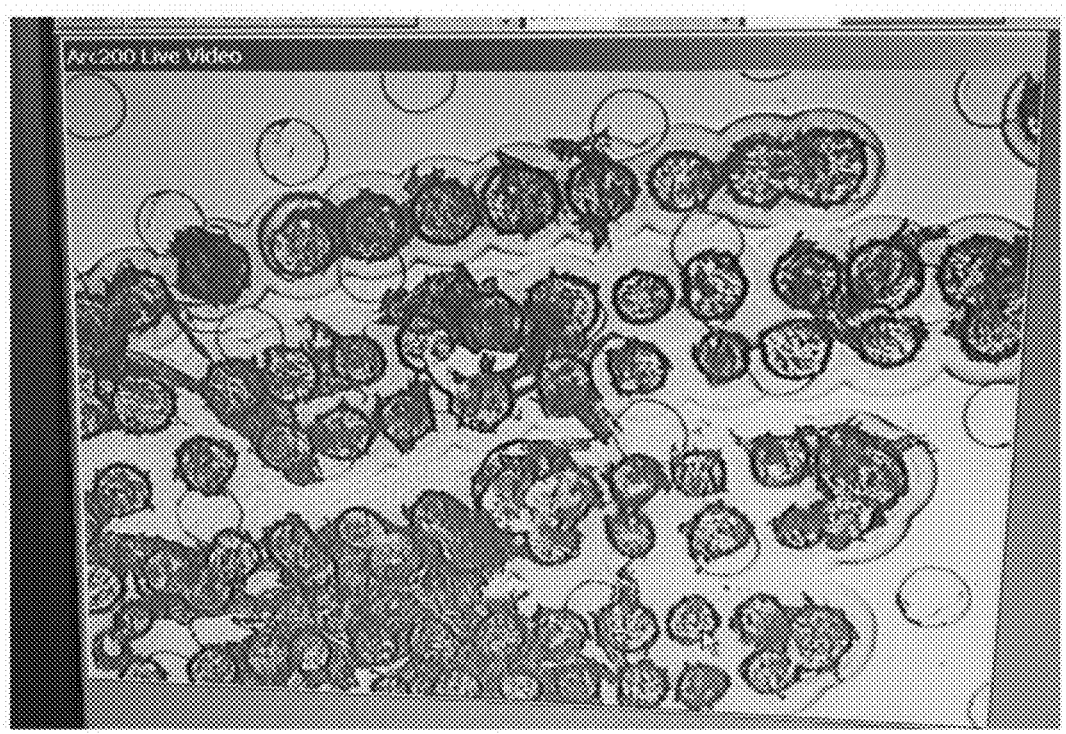

FIGS. 5E and 5F are representative microscopic images (100× magnification) of captured cells using the micropatterned surfaces of FIGS. 5A and 5B. Cancer cells were collected from colorectal cancer invading dense collagenous stroma within an 8 micron Hematoxylin stained tissue section mounted on an uncharged microscope slide. Without the use of the micropatterned surface, the capture of tumor cells from this case was zero percent. Both large and smaller micropatterns (5 microns (FIG. 5E) versus 10 microns (FIG. 5F)) captured greater than 95% of the desired tumor cells demonstrating the large improvement in capture efficiency afforded by the disclosed apparatus and method. Thus, in contrast to existing microdissection methods, it is contemplated that the micropatterned thermoplastic films disclosed herein can effectively capture human tumor cells within dense fibrotic collagenous stroma.

A similar strategy can be utilized to create needle shaped structures instead of cylindrical pillars. Alternatively, IR sensitive polymer can be selectively deposited at the tip of PDMS needles. By fabricating molds containing conical wells, PDMS or plastic blocks with needle shaped structures can be easily created. Subsequently placing these needle shaped features in contact with a film of IR polymer at a temperature slightly higher than its liquid transition temperature will deposit a layer of the IR material on PDMS needles.

Nanoparticles (and other particles) can be immobilized on projection (e.g., pillar) tips or other surface modification can be performed. Proteins of interest can be adsorbed onto the PDMS surface by microcontact printing for which complementary ligands can be functionalized on nanoparticles. Placing a drop of nanoparticles on the functionalized surface can allow them to adhere specifically at the tip of projections (e.g., pillars or needles) where proteins were predeposited.

Exemplary Aspects

In view of the described devices, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: An apparatus comprising: a patterned thermoplastic film having: a first surface; and a plurality of projections attached to and extending outwardly from the first surface, wherein the projections form a pattern on the thermoplastic film.

Aspect 2: The apparatus of aspect 1, wherein the projections extend outwardly from the first surface of the patterned thermoplastic film relative to an axis that is substantially perpendicular to the first surface.

Aspect 3: The apparatus of aspect 1 or aspect 2, wherein the projections are continuous with, and integrally formed with, the first surface of the patterned thermoplastic film.

Aspect 4: The apparatus of any one of aspects 1-3, wherein the pattern is an array of projections.

Aspect 5: The apparatus of any one of aspects 1-4, wherein at least one of the projections has a consistent diameter.

Aspect 6: The apparatus of any one of aspects 1-5, wherein at least one of the projections has a variable diameter.

Aspect 7: The apparatus of aspect 6, wherein at least one of the projections is a microneedle that has a diameter that decreases moving away from the first surface of the patterned thermoplastic film.

Aspect 8: The apparatus of aspect 6, wherein at least one of the projections is a microsphere.

Aspect 9: The apparatus of aspect 8, wherein the microsphere comprises a hydrogel.

Aspect 10: The apparatus of any one of aspects 1-9, wherein each projection defines at least one tip, and wherein at least one tip of at least one of the projections is coated with one or more particles.

Aspect 11: The apparatus of aspect 10, wherein the particles are nanoparticles.

Aspect 12: The apparatus of aspect 10, wherein the particles are microparticles.

Aspect 13: The apparatus of any one of aspects 10-12, wherein at least one particle comprises a hydrogel.

Aspect 14: The apparatus of any one of aspects 10-13, wherein at least one particle comprises dissociating cross-links.

Aspect 15: The apparatus of aspect 14, wherein the dissociating cross-links dissociate upon irradiation with electromagnetic radiation in the UV or IR spectrum.

Aspect 16: The apparatus of any one of aspects 10-13, wherein at least one particle comprises reversible cross-links.

Aspect 17: The apparatus of aspect 16, wherein the reversible cross-links are cleaved upon irradiation with electromagnetic radiation in the UV or IR spectrum.

Aspect 18: The apparatus of any one of aspects 10-17, wherein at least one particle comprises an outer shell and an inner core.

Aspect 19: The apparatus of aspect 18, wherein the inner core is adhesive with respect to a cell surface.

Aspect 20: The apparatus of aspect 18 or aspect 19, wherein the shell is non-adhesive with respect to a cell surface.

Aspect 21: The apparatus of any one of aspects 10-17, wherein, in the absence of irradiation with electromagnetic radiation in the UV or IR spectrum, at least one particle is adhesive with respect to a cell surface.

Aspect 22: The apparatus of aspect 21, wherein the at least one particle is non-adhesive with respect to a cell surface upon irradiation with electromagnetic radiation in the UV or IR spectrum.

Aspect 23: The apparatus of any one of aspects 1-22, wherein the patterned thermoplastic film further comprises an adsorptive substance.

Aspect 24: The apparatus of aspect 23, wherein the adsorptive substance is an infrared napthalocyanine dye.

Aspect 25: The apparatus of aspect 23, wherein the adsorptive substance is tin(IV) 2,3-naphthalocyanine dichloride; silicon(IV) 2,3-naphthalocyanine dihydroxide; silicon (IV) 2,3-naphthalocyanine dioctyloxide; or vanadyl 2,11,20,29-tetra-tert-butyl-2,3-naphthalocyanine, or combinations thereof.

Aspect 26: The apparatus of any one of aspects 1-25, wherein the patterned thermoplastic film comprises an ethyl vinyl acetate polymer, a vipolyurethane polymer; a polyvinyl acetate polymer; an ethylene-methyl acrylate polymer; a polycarbonate polymer; an ethylene-vinyl alcohol copolymer; a polypropylene polymer; or an expandable or general purpose polystyrene polymer, or combinations thereof.

Aspect 27: A method for laser capture microdissection, comprising the steps of: (a) placing the apparatus of any one of aspects 1-26 in contact with a tissue sample, and (b) irradiating the apparatus in contact with the tissue sample with electromagnetic energy or wavelengths in the UV or IR spectrum.

Aspect 28: The method of aspect 27, wherein the patterned thermoplastic film contacts a first surface of the tissue sample, and wherein an opposed second surface of the tissue sample rests on a coating of microparticles or nanoparticles that is positioned on an upper surface of a glass slide.

Aspect 29: A kit comprising the apparatus of any one of aspects 1-26, and instructions for the use of the apparatus in laser capture microdissection.

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A method for laser capture microdissection, comprising the steps of:
    (a) placing a patterned thermoplastic film in contact with a tissue sample, the patterned thermoplastic film having a first surface and a plurality of projections attached to and extending outwardly from the first surface, wherein the projections form a pattern on the thermoplastic film; and
    (b) irradiating the patterned thermoplastic film in contact with the tissue sample with electromagnetic energy or wavelengths in the UV or IR spectrum.

2. The method of claim 1, wherein the patterned thermoplastic film contacts a first surface of the tissue sample, and wherein an opposed second surface of the tissue sample rests on a coating of microparticles or nanoparticles that is positioned on an upper surface of a glass slide.

3. The method of claim 1, wherein the projections extend outwardly from the first surface of the patterned thermoplastic film relative to an axis that is substantially perpendicular to the first surface.

4. The method of claim 1, wherein the projections are continuous with, and integrally formed with, the first surface of the patterned thermoplastic film.

5. The method of claim 1, wherein the pattern is an array of projections.

6. The method of claim 1, wherein at least one of the projections has a consistent diameter.

7. The method of claim 1, wherein at least one of the projections has a variable diameter.

8. The method of claim 7, wherein at least one of the projections is a microneedle that has a diameter that decreases moving away from the first surface of the patterned thermoplastic film.

9. The method of claim 7, wherein at least one of the projections is a microsphere.

10. The method of claim 9, wherein the microsphere comprises a hydrogel.

11. The method of claim 1, wherein each projection defines at least one tip, and wherein at least one tip of at least one of the projections is coated with one or more particles, wherein the particles are microparticles, nanoparticles, or combinations thereof.

12. The method of claim 11, wherein at least one particle comprises a hydrogel.

13. The method of claim 11, wherein at least one particle comprises dissociating cross-links, wherein the dissociating cross-links dissociate upon irradiation with electromagnetic radiation in the UV or IR spectrum.

14. The method of claim 11, wherein at least one particle comprises reversible cross-links, wherein the reversible cross-links are cleaved upon irradiation with electromagnetic radiation in the UV or IR spectrum.

15. The method of claim 11, wherein at least one particle comprises an outer shell and an inner core.

16. The method of claim 15, wherein the inner core is adhesive with respect to a cell surface, and wherein the shell is non-adhesive with respect to a cell surface.

17. The method of claim 11, wherein, at least one particle is:
    (a) adhesive with respect to a cell surface in the absence of irradiation with electromagnetic radiation in the UV or IR spectrum; and
    (b) non-adhesive with respect to a cell surface upon irradiation with electromagnetic radiation in the UV or IR spectrum.

18. The method of claim 1, wherein the patterned thermoplastic film further comprises an adsorptive substance, and wherein the adsorptive substance is an infrared napthalocyanine dye; tin(IV) 2,3-naphthalocyanine dichloride; silicon(IV) 2,3-naphthalocyanine dihydroxide; silicon (IV) 2,3-naphthalocyanine dioctyloxide; or vanadyl 2,11,20,29-tetra-tert-butyl-2,3-naphthalocyanine, or combinations thereof.

19. The method of claim 1, wherein the patterned thermoplastic film comprises an ethyl vinyl acetate polymer, a vipolyurethane polymer; a polyvinyl acetate polymer; an ethylene-methyl acrylate polymer; a polycarbonate polymer; an ethylene-vinyl alcohol copolymer; a polypropylene polymer; or an expandable or general purpose polystyrene polymer, or combinations thereof.

* * * * *